(12) United States Patent
Lee et al.

(10) Patent No.: US 8,881,575 B2
(45) Date of Patent: Nov. 11, 2014

(54) APPARATUS FOR COLLECTING GAS SAMPLE IN FOAM, AND ANALYSIS METHOD USING THE SAME

(75) Inventors: Jin-Bok Lee, Daejeon (KR); Jin-Seog Kim, Daejeon (KR); Dong-Min Moon, Daejeon (KR); Kwang-Sup Kim, Daejeon (KR); Jeong-Soon Lee, Gwangju (KR)

(73) Assignee: Korea Research Institute of Standards and Science (KR)

( * ) Notice: Subject to any disclaimer, the term of this patent is extended or adjusted under 35 U.S.C. 154(b) by 808 days.

(21) Appl. No.: 13/139,635

(22) PCT Filed: Dec. 15, 2009

(86) PCT No.: PCT/KR2009/007509
§ 371 (c)(1),
(2), (4) Date: Jun. 14, 2011

(87) PCT Pub. No.: WO2010/071348
PCT Pub. Date: Jun. 24, 2010

(65) Prior Publication Data
US 2011/0247395 A1    Oct. 13, 2011

(30) Foreign Application Priority Data

Dec. 15, 2008   (KR) .................. 10-2008-0127179

(51) Int. Cl.
| | |
|---|---|
| *G01N 7/00* | (2006.01) |
| *G01N 7/14* | (2006.01) |
| *G01N 1/28* | (2006.01) |
| *G01N 1/22* | (2006.01) |

(52) U.S. Cl.
CPC .............. *G01N 7/14* (2013.01); *G01N 1/286* (2013.01); *G01N 1/22* (2013.01); *G01N 2001/2866* (2013.01)
USPC ...................................... 73/31.04

(58) Field of Classification Search
CPC ... G01N 1/22; G01N 2001/2866; G01N 7/14; B29B 17/02; B29B 17/04; B29B 17/0404
USPC ............................. 73/31.04; 241/29
See application file for complete search history.

(56) References Cited

U.S. PATENT DOCUMENTS

| | | | |
|---|---|---|---|
| 5,431,347 A | 7/1995 | Hayashi et al. | |
| 6,036,124 A | 3/2000 | Takahashi et al. | |
| 2001/0013558 A1* | 8/2001 | Miyamoto et al. | 241/29 |
| 2004/0145071 A1* | 7/2004 | Yotsumoto et al. | 264/37.14 |

FOREIGN PATENT DOCUMENTS

| | | |
|---|---|---|
| JP | 07288098 | 10/1995 |
| JP | 08-085114 | 4/1996 |

(Continued)

OTHER PUBLICATIONS

English Machine Translation of Noriaki et al., JP 08-085114, Apr. 1996, Translated May 2014.*

(Continued)

*Primary Examiner* — Hezron E Williams
*Assistant Examiner* — David Z Huang
(74) *Attorney, Agent, or Firm* — Cantor Colburn LLP

(57) ABSTRACT

Provided are an apparatus for collecting gas samples in a foam and an analysis method using the same, and more particularly, to an apparatus for collecting gas samples in a foam in which the foam is grinded, such that the gas sample in the foam may be effectively collected, and pressure before and after collection of the gas samples may be measured to thereby increase accuracy of gas analysis, such that characteristics of the foam may be more accurately evaluated, and an analysis method using the same.

11 Claims, 8 Drawing Sheets

(56) References Cited

FOREIGN PATENT DOCUMENTS

| JP | 2002-096056 | 4/2002 |
| KR | 1994-0025734 | 12/1994 |
| KR | 10-2000-0004865 | 1/2000 |

OTHER PUBLICATIONS

International Search Report—PCT/KR2009/007509 dated Jul. 28, 2010.

* cited by examiner

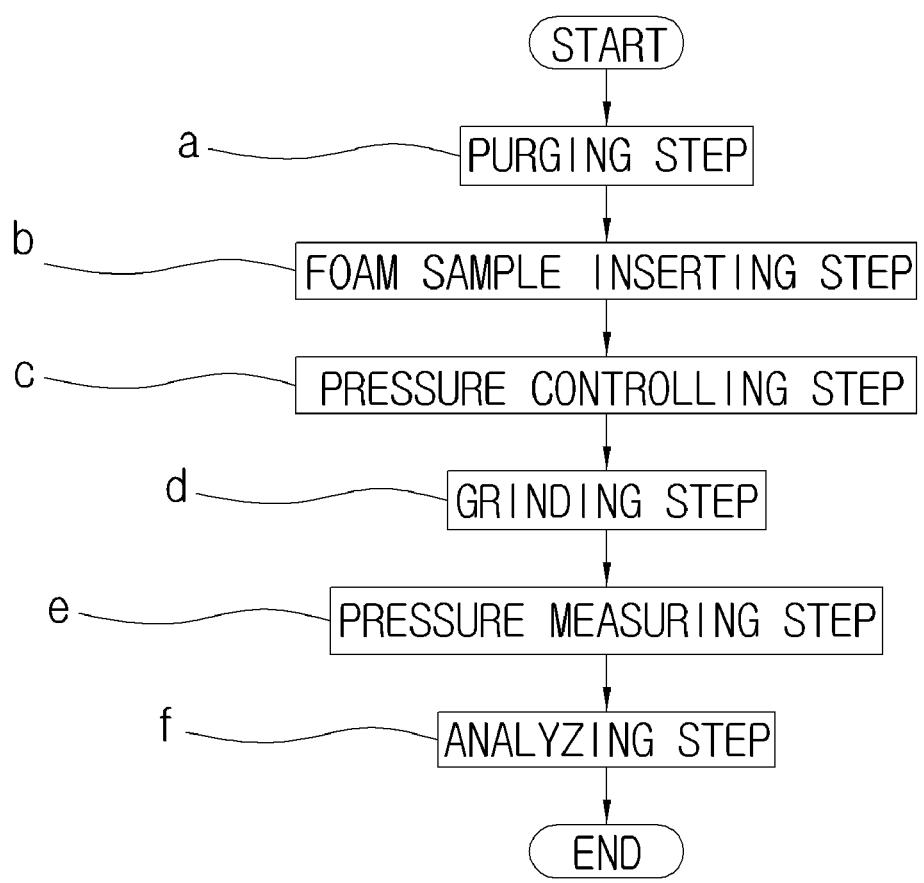

APPARATUS FOR COLLECTING GAS SAMPLE IN FOAM, AND ANALYSIS METHOD USING THE SAME

TECHNICAL FIELD

The present invention relates to an apparatus for collecting gas samples in a foam and an analysis method using the same, and more particularly, to an apparatus for collecting gas samples in a foam in which the foam is grinded, such that the gas sample in the foam may be effectively collected, and pressure before and after collection of the gas samples may be measured to thereby increase accuracy of gas analysis, such that characteristics of the foam may be more accurately evaluated, and an analysis method using the same.

BACKGROUND ART

A foam, which means a form in which a plurality of cells including gas therein or maintained in a vacuum state are formed, are formed using various materials throughout various industries.

The foam has cells formed therein through a reaction between a foam forming material and foaming gas. Since characteristics of the foam are significantly changed according to a size of the cell in the foam and the kind and amount of gas included in the cell therein, it is very important to collect gas in the foam and perform quantitative and qualitative analysis.

As a method of collecting gas samples in a foam according to the related art, a method of cutting a foam using a blade in a closed module, collecting gas in a cylinder and then analyzing the gas was suggested by Svantrom and Ramnas thirteen years ago.

In the above-mentioned method, a specific portion of the foam is cut and the gas in the cut cell is collected. However, even though a plurality of sample cut portions of the foam has the same shape, there is a difference in the amount of the collected gas due to irregularity of the cells in the foam. In addition, even though the number of cutting increases, it is impossible to completely destroy the foam due to the resilience of an organic foam. Therefore, it is difficult to completely collect gas included in the cell in the foam.

That is, even when a repetitive test is performed using the same foam sample, an error occurs in a result value of the gas collected by the above-mentioned method, thereby deteriorating the reliability of the test.

Meanwhile, in the case of a urethane foam that is being widely used as a heat insulator among foams, as time passes, thermal conductivity is increased to thereby deteriorate heat insulating performance, which is determined by foam gas and residual gas (oxygen, nitrogen, carbon dioxide, or the like) existing in gas included in the cell in the foam.

More specifically, in the case of the urethane foam, the gas including carbon dioxide in the cell in the foam is rapidly expanded in the early stage of formation thereof to thereby be leaked to the outside of the urethane foam. When the urethane foam is exposed in the air for a long time, gas such as nitrogen and oxygen in the air is diffused into the foam, thereby reducing the heat insulating performance in the foam.

Therefore, a process of collecting and analyzing the gas sample in the urethane foam is a main factor of determining performance of the urethane form. Particularly, in the case in which a heat insulator is used as a construction material, when the heat insulating performance is deteriorated with the passage of time, primarily, appropriate heat insulation is not performed to thereby cause energy to be wasted, and, secondarily, a high cost and a long period of time are required due to a difficulty in a replacement process of the heat insulator, that is, a process of destroying an inner wall and performing reconstruction in order to replace the heat insulator, or the like, to thereby cause energy to be additionally wasted.

Furthermore, the heat insulation is a most basic method for reducing energy consumption of a building. In accordance with the recent increase in interest in the environment and energy due to an increase in energy usage amount and rising in oil prices, a necessity for efficiently managing the energy throughout various industries, such as a construction industry, a refrigerator industry, an automobile industry, and the like, has increased.

DISCLOSURE

Technical Problem

An object of the present invention is to provide an apparatus for collecting gas samples in a foam in which the gas sample in the foam may be easily collected by grinding the foam including a plurality of cells irregularly formed therein, and reliability of a test may be increased reducing an error, and an analysis method using the same.

Another object of the present invention is to provide an apparatus for collecting gas samples in a foam in which characteristics of the foam may be more accurately evaluated by measuring pressure before and after collection of gas samples, and an analysis method using the same.

Technical Solution

In one general aspect, an apparatus 1000 of collecting gas samples in a foam F includes: a body 100 having a foam receiving part 121 formed therein so that the foam F is received therein; a grinding part 200 formed to contact one side of the foam F in the body 100, thereby grinding the foam F; a pressing part 300 formed to contact the other side of the foam F in the body 100, thereby pressing the foam F toward the grinding part 200; a purge gas injecting part 400 formed at one side of the body 100 to thereby inject purge gas into the body 100 and having a first valve 430 formed therein; a gas discharging part 500 formed at one side of the body 100 to thereby discharge gas in the body 100 to the outside and having a second valve 510 formed therein; and a pressure gauge 600 measuring pressure in the body 100.

The body 100 may be formed by coupling a first body 110 including the grinding part 200, a second body 120 having the foam receiving part 121 formed therein, and a third body 130 including the pressing part 300.

After the second and third bodies 120 and 130 are decoupled from each other, the foam receiving part 121 of the second body 120 may have a foam sample extracting part 140 inserted thereinto, the foam sample extracting part 140 extracting a foam F sample to thereby include the foam F therein.

The foam sample extracting part 140 may have a protrusion part 141 formed so as to protrude outwardly from one side end thereof, and the second body 120 may have a stepped part 122 formed therein, the stepped part 122 having the protrusion part 141 seated therein to thereby limit an insertion depth of the foam sample extracting part 140.

The grinding part 200 may include a grinding plate 210, a grinding plate support part 220 supporting the grinding plate 210, and a grinding plate driving part 230 connected to the grinding plate support part 220 to thereby rotate the grinding plate 210.

The second body 120 may be positioned so that the foam receiving part 121 is eccentric to the grinding plate 210.

The pressing part 300 may include a pressing shaft 310, a rail 330 having the first body 110 fixed thereto, a pressing shaft fixing part 320 connected to the rail 330 and fixing the pressing shaft 310 thereto, and a pressing shaft driving part (not shown) moving the pressing shaft 310 and the pressing shaft fixing part 320 along the rail 330.

The purge gas injecting part 400 may be formed in the second body 120, and the gas discharging part 500 may be formed in the third body 130.

The purge gas injecting part 400 may further include a purge gas storing part 410 and a flow controlling part 420.

The gas discharging part 500 may be directly connected to an analyzing device 700.

In another general aspect, a method of analyzing gas samples in a foam F using the apparatus 1000 as described above includes: a) a purging step of opening the first valve 430 of the purge gas injecting part 400 and the second valve 510 of the gas discharging part 500, thereby allowing the purge gas to purge the inside of the body 100; b) a foam F sample inserting step of inserting the foam sample extracting part 140 extracting the foam (F) sample into the foam receiving part 121 of the second body 120 after the second and third bodies 120 and 130 are decoupled from each other; c) a pressure controlling step of controlling pressure in the body to be in an atmospheric pressure state after the second and third bodies 120 and 130 are coupled to each other; d) a grinding step of grinding the foam F by operating the pressing part 300 and the grinding part 200; e) a pressure measuring step of controlling a position of the pressing part 300 to be in an initial state to thereby allow a space in the body 100 to be the same as a state before the grinding step and then measuring the pressure using the pressure gauge 600; and f) an analyzing step of analyzing the gas samples in the foam by connecting the analyzing device 700 to the gas discharging part 500 and then opening the second valve 510.

Advantageous Effects

Therefore, with the apparatus for collecting gas samples in a foam and the analysis method using the same according to the present invention, the foam including a plurality of cells irregularly formed therein is grinded, thereby making it possible to easily collect the gas sample in the foam, and an error is reduced, thereby making it possible to increase reliability of a test.

In addition, with the apparatus for collecting gas samples in a foam and the analysis method using the same according to the present invention, pressure before and after collection of gas samples may be measured, thereby making it possible to more accurately evaluate characteristics of the foam.

DESCRIPTION OF DRAWINGS

The above and other objects, features and advantages of the present invention will become apparent from the following description of preferred embodiments given in conjunction with the accompanying drawings, in which:

FIG. 8 is a flow chart of a method of analyzing gas samples in a foam according to the present invention.

DETAILED DESCRIPTION OF MAIN ELEMENTS

| 1000: APPARATUS FOR COLLECTING GAS SAMPLES IN FOAM ACCORDING TO THE PRESENT INVENTION | |
|---|---|
| F: FOAM | |
| 100: BODY | |
| 110: FIRST BODY | 120: SECOND BODY |
| 121: FORM RECEIVING PART | 122: STEPPED PART |
| 130: THIRD BODY | |
| 140: FOAM SAMPLE EXTRACTING PART | 141: PROTRUSION PART |
| 200: GRINDING PART | 210: GRINDING PLATE |
| 220: GRINDING PLATE SUPPORT | 230: GRINDING PLATE DRIVING PART |
| 300: PRESSING PART | 310: PRESSING SHAFT |
| 320: PRESSING SHAFT FIXING PART | 330: RAIL |
| 400: PURGE GAS INJECTING PART | 410: PURGE GAS STORING PART |
| 420: FLOW CONTROLLING PART | 430: FIRST VALVE |
| 500: GAS DISCHARGING PART | 510: SECOND VALVE |
| 600: PRESSURE GAUGE | |
| 700: ANALYZING DEVICE | |

BEST MODE

Hereinafter, an apparatus 1000 for collecting gas samples in a foam F and an analysis method using the same according to the present invention having the above-mentioned characteristics will be described in detail with reference to the accompanying drawings.

Figure 1:
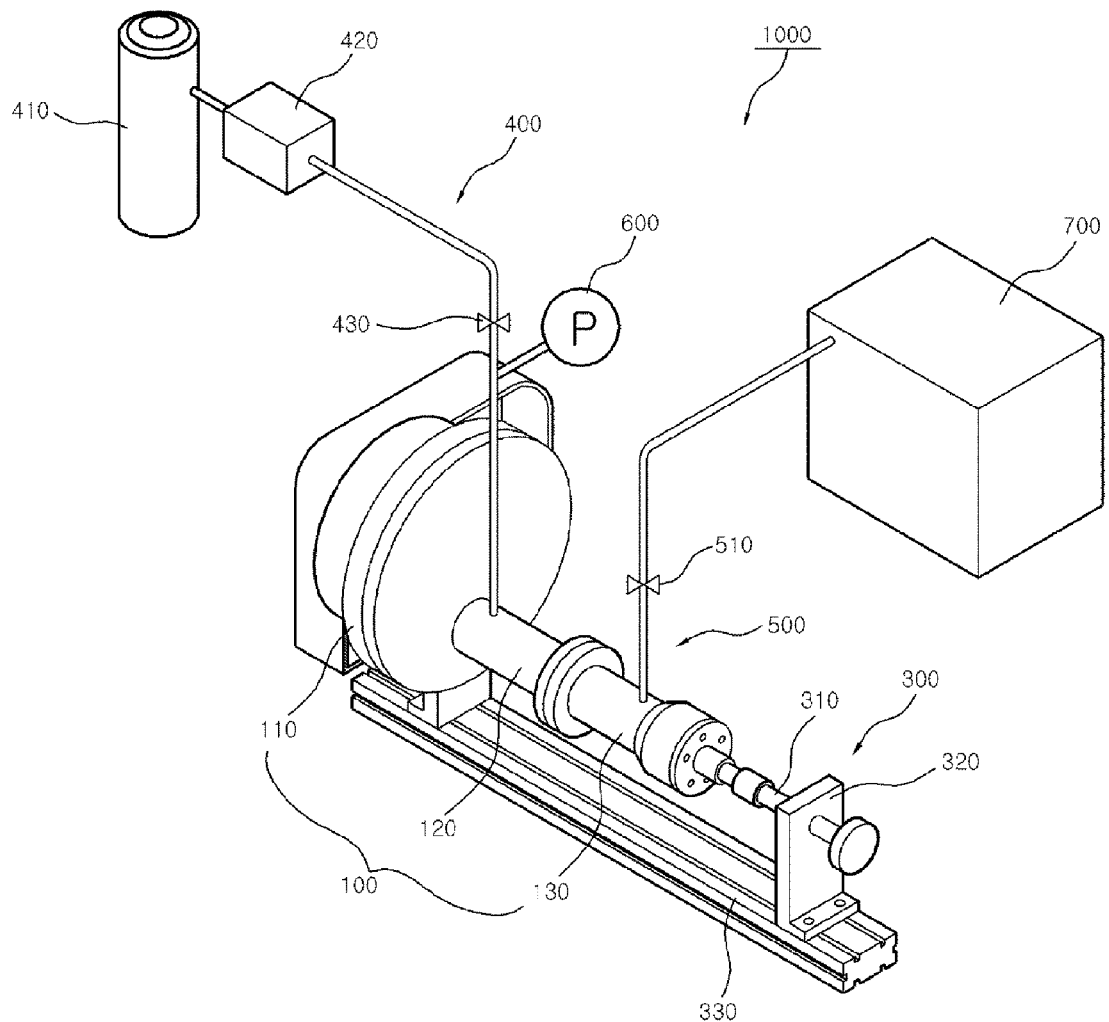
FIGS. 1 to 3 are, respectively, a perspective view, an exploded perspective view, and a cross-sectional view of an apparatus for collecting gas samples in a foam according to the present invention.
Figure 2:
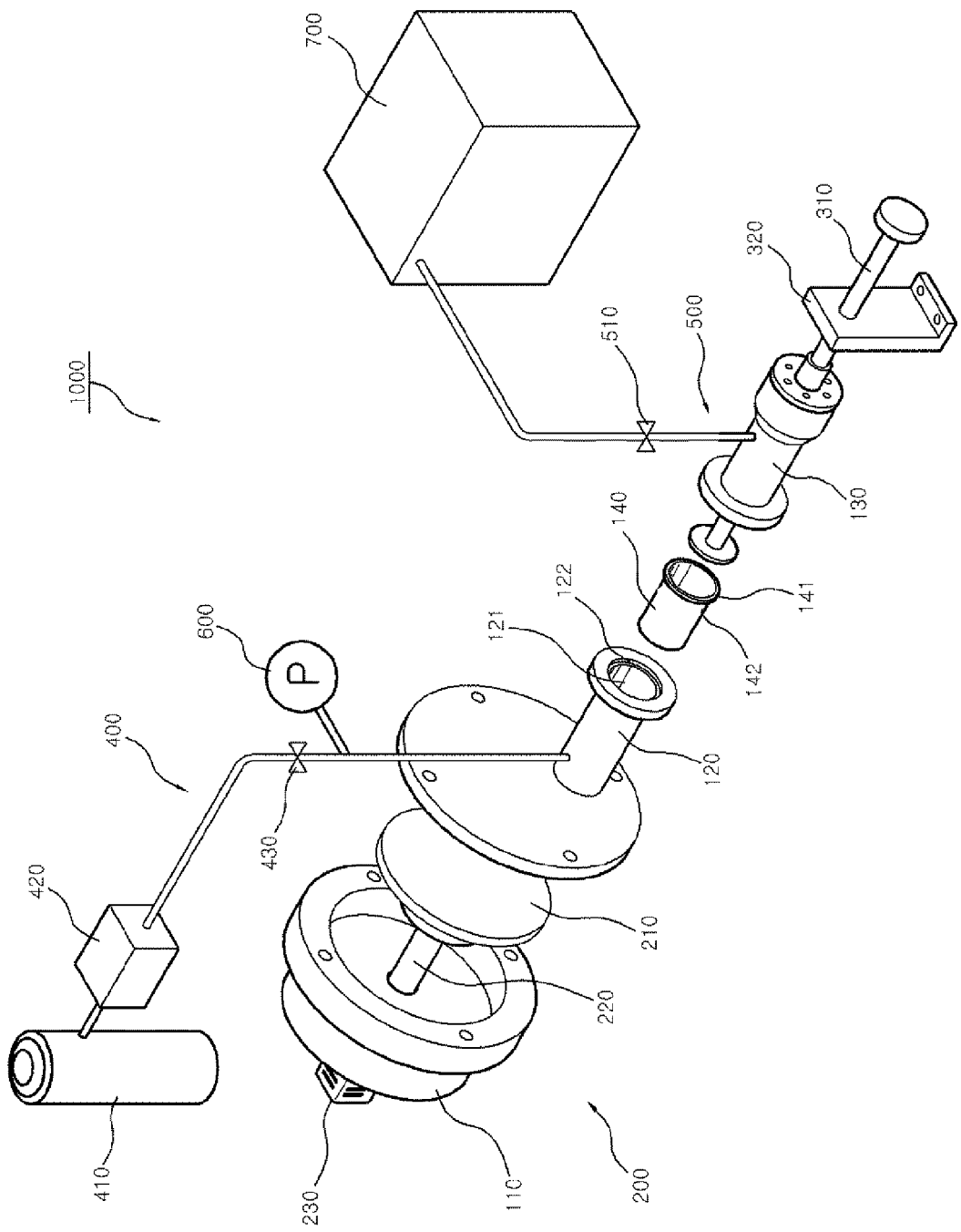
Figure 3:
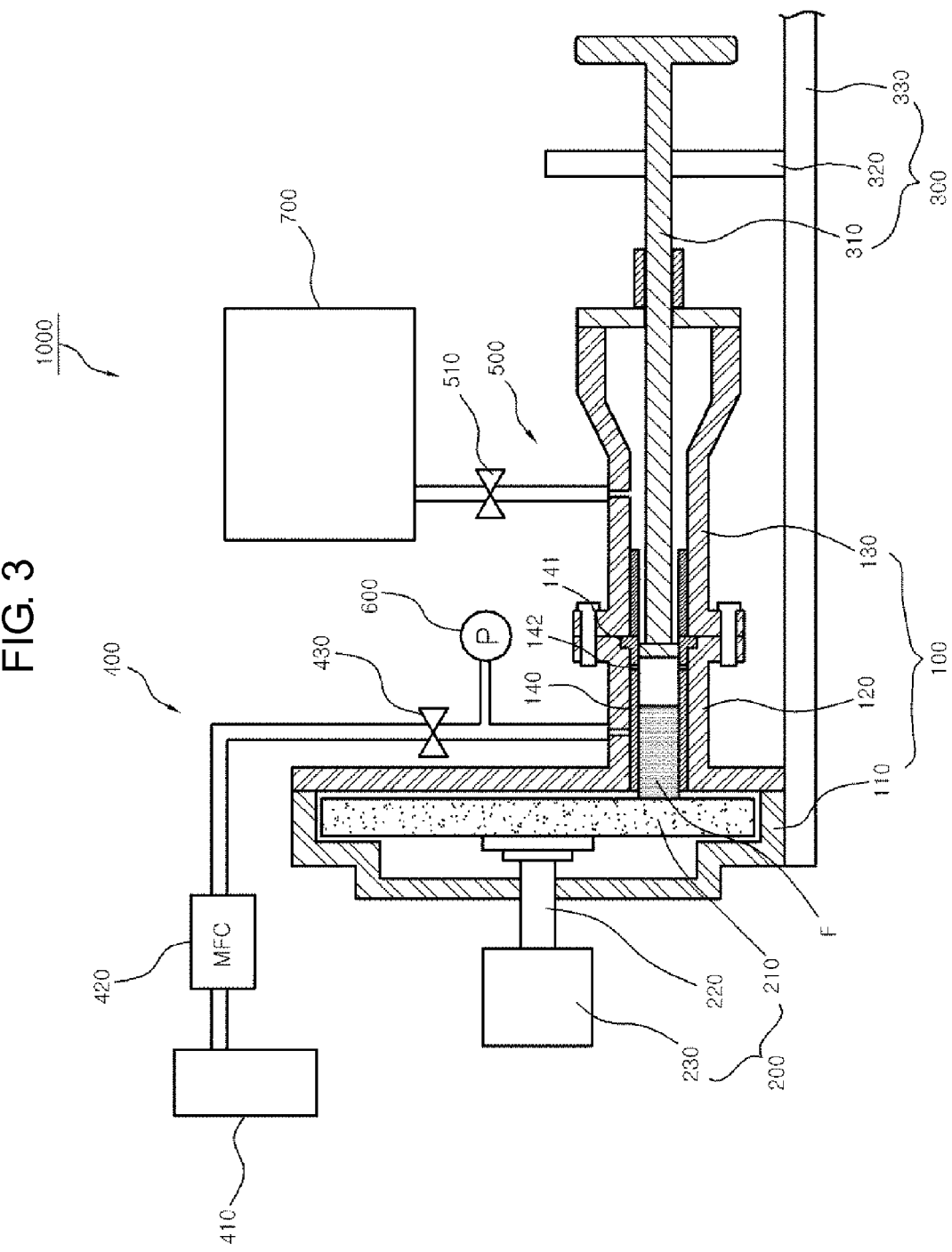
Figure 4:
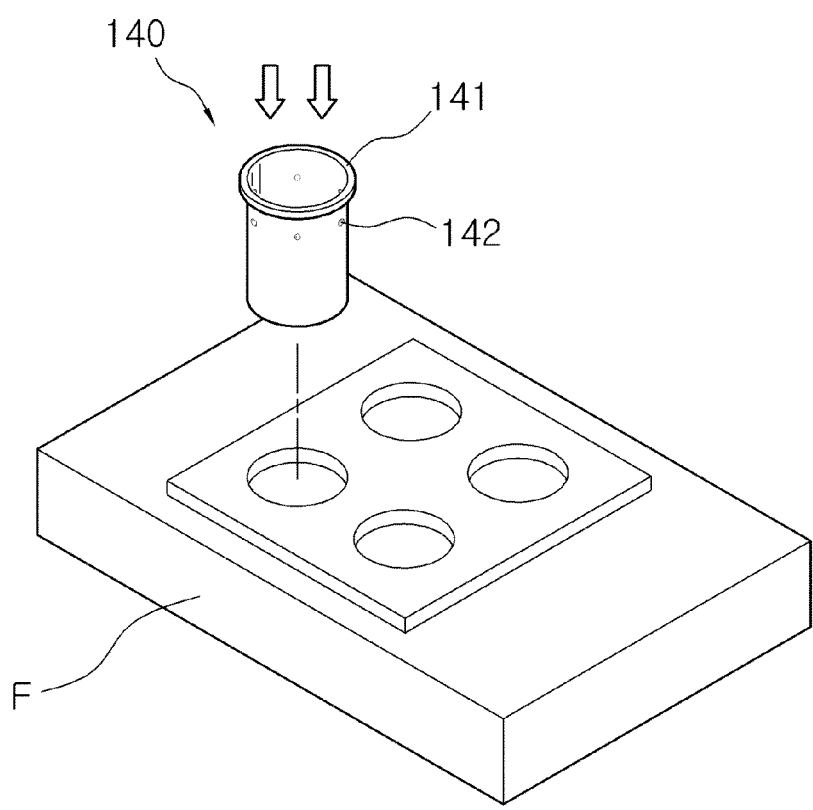
FIG. 4 is a view showing an example in which a foam sample extracting part of an apparatus for collecting gas samples in a foam according to the present invention extracts foam samples.
Figure 5:
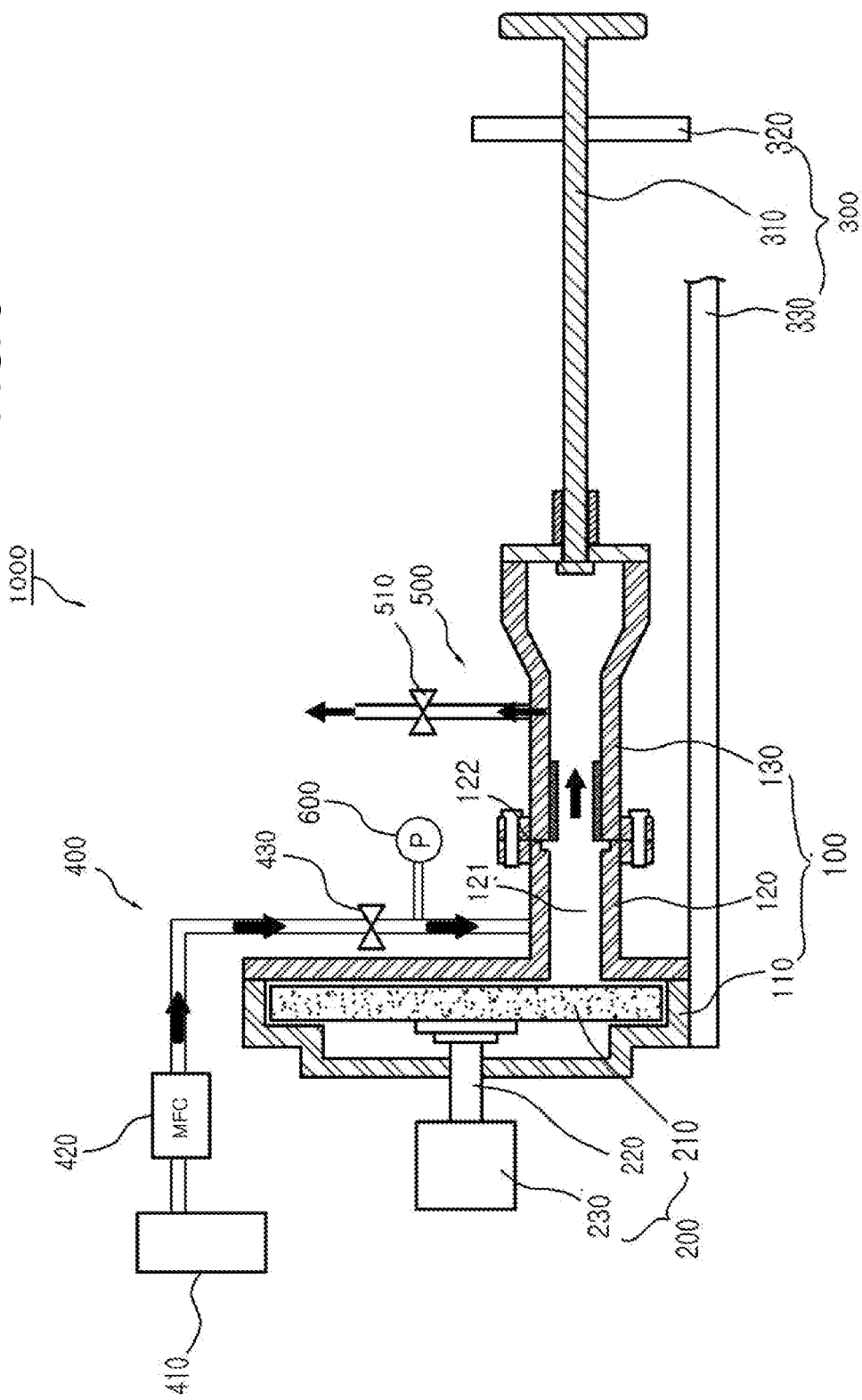
FIGS. 5 to 7 are views showing an operation of an apparatus for collecting gas samples in a foam according to the present invention.
Figure 6:
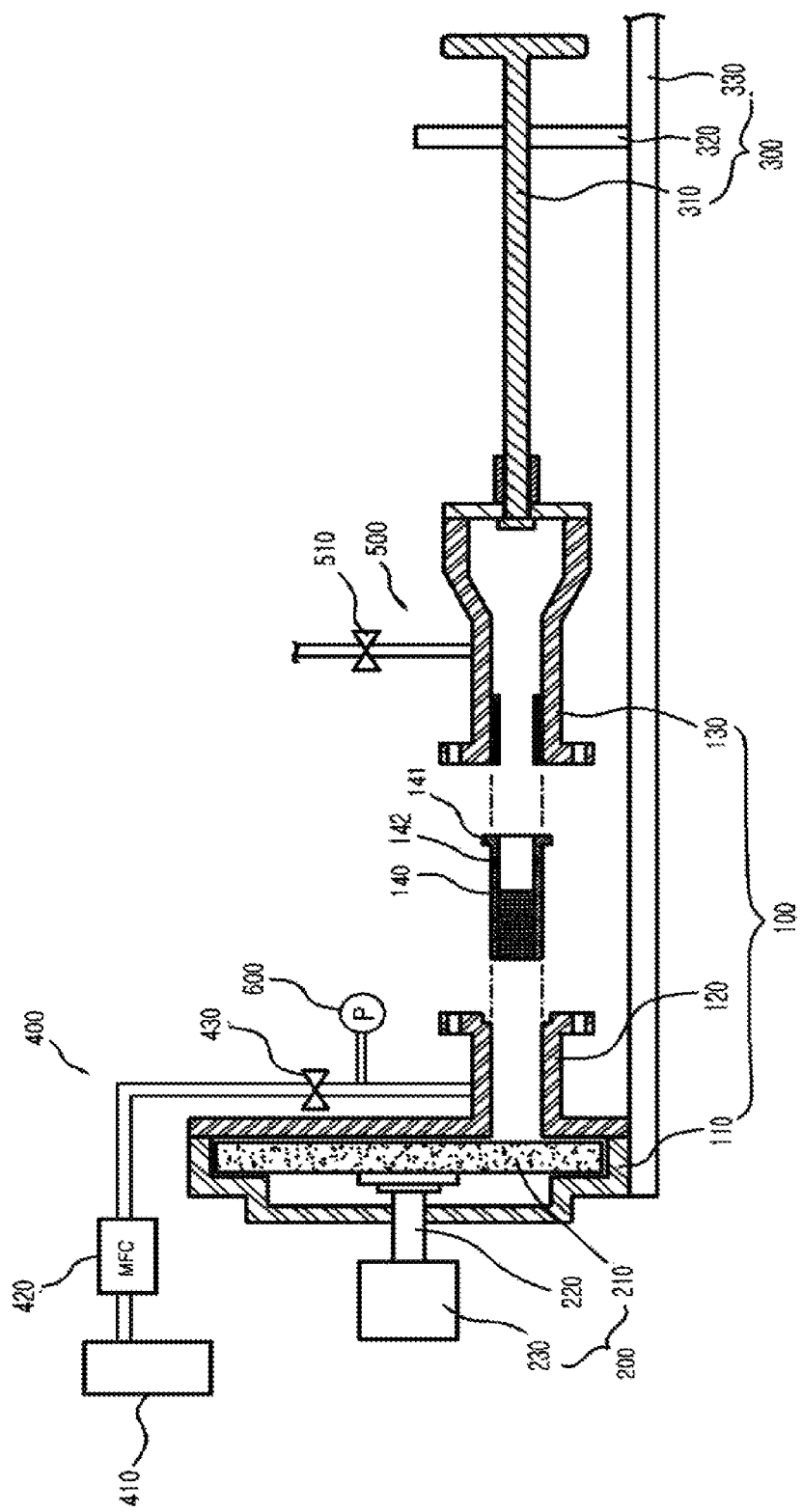
Figure 7:
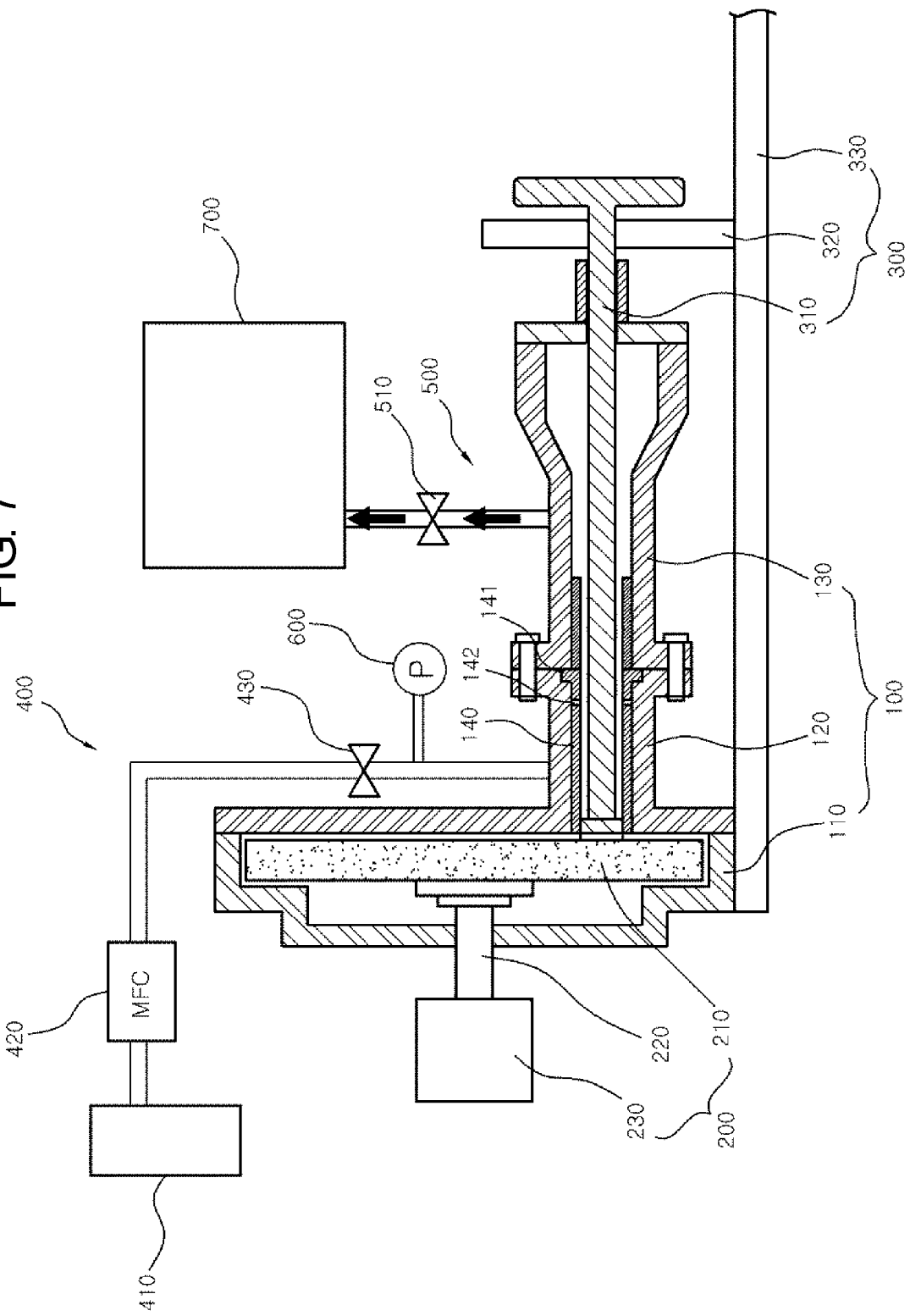

FIGS. 1 to 3 are, respectively, a perspective view, an exploded perspective view, and a cross-sectional view of an apparatus 1000 for collecting gas samples in a foam F according to the present invention; FIG. 4 is a view showing an example in which a foam sample extracting part 140 of an apparatus 1000 for collecting gas samples in a foam F according to the present invention extracts foam F samples; FIGS. 5 to 7 are views showing an operation of an apparatus 1000 for collecting gas samples in a foam F according to the present invention; and FIG. 8 is a flow chart of a method of analyzing gas samples in a foam F.

An apparatus 1000 for collecting gas samples in a foam F according to the present invention is configured to include a body 100, which is a basic component thereof, a grinding part 200, a pressing part 300, a purge gas injecting part 400, a gas discharging part 500, and a pressure gauge 600.

The body 100 includes a foam receiving part 121 of which a predetermined area is hollow so that the foam F may be received therein, and includes some components of the grinding part 200 and the pressing part 300 therein.

The body 100 may be easily produced and assembled, and is preferably formed by separately manufacturing a first body 110 including the grinding part 200, a second body 120 having the foam receiving part 121 formed therein, and a third body 130 including the pressing part 300 and then assembling them so that the foam F may be easily inserted thereinto.

After the apparatus is assembled, the body 100 should be maintained in an airtight state so that gas therein is not discharged to the outside or external gas does not flow therein.

When the foam F is cut to have a predetermined size in order to perform a test, cells positioned at a cut surface of the foam F are destroyed, such that gas thereof is discharged to the outside. Therefore, in the apparatus 1000 for collecting gas samples in a foam F according to the present invention, a frame is formed on the foam F and a separate foam sample extracting part 140 is inserted thereinto, thereby making it possible to extract a foam sample, as shown in FIG. 4.

In addition, hollow holes 142 of which a predetermined area is hollow are formed in an outer surface of the foam F, such that purge gas injected by the purge gas injecting part 400 may smoothly flow therein. When a process of extracting the foam sample is performed, a separate member is connected to a fixing member inserted into the hollow hole 142 to increase a catchable area, thereby making it possible to allow the process for extracting the foam sample to be more easily performed.

The separate member and the fixing member are connected to each other only when the foam sample extracting unit 140 extracts the foam sample and are disconnected after it extracts the foam sample.

In addition, it is preferable that the foam sample extracting part 140 that has extracted the foam F sample is inserted into the foam receiving part 121 of the second body 120 as it is, thereby simplifying the process of extracting the foam F sample and minimizing the discharging of gas from the inside of the foam F (See FIG. 6).

The entirety of an analyzing method including the method for collecting gas samples in a foam F will be again described below.

In addition, the foam sample extracting part 140 has a protrusion part 141 formed to partially protrude outwardly from an end thereof, and the foam receiving part 121 of the second body 120 has a stepped part 122 formed therein, wherein the stepped part 122 has the protrusion part 141 seated therein to thereby limit an insertion depth of the foam sample extracting part 140.

The grinding part 200 is included in the first body 110 and is formed to contact one side of the foam F included in the second body 120.

The grinding part 200 may include various units capable of grinding the foam F; however, it may preferably include a grinding plate 210, a grinding plate support part 220 supporting the grinding plate 210, and a grinding plate driving part 230 connected to the grinding plate support part 220 to thereby rotate the grinding plate 210.

The grinding plate 210 contacts the foam F to thereby grind the foam F. Various materials including a sand paper, a diamond grinding sheet, or the like, may be used as the grinding plate. Here, the grinding plate 210 may be appropriately selected and used according to the hardness of the foam F.

Here, in order to effectively grind the foam F, the foam receiving part 121 of the second body 120 preferably has a position controlled so that it is eccentric to one side of the grinding plate 210 (the center axis of the foam F is out of the center axis of the grinding plate 210).

The pressing part 300 presses the foam F toward the grinding part 200 to thereby allow the foam F to be effectively grinded. Various units capable of appropriately pressing the foam F may be used as the pressing part 300.

In the apparatus 1000 for collecting gas samples in a foam F according to the present invention, the pressing part 300 may be configured to include a pressing shaft 310, a rail 330 having the first body 110 fixed thereto, a pressing shaft fixing part 320 connected to the rail 330 and fixing the pressing shaft 310 thereto, and a pressing shaft driving part (not shown) moving the pressing shaft 310 and the pressing shaft fixing part 320 along the rail 330, as shown in FIGS. 1 to 3.

In this configuration, as described above, the stepped part 122 is formed in the foam receiving part 121 and the protrusion part 140 is formed on the foam sample extracting part 140, such that when the pressing shaft 310 of the pressing part 300 moves, only the foam F sample in the foam sample extracting part 140 moves.

One side end of the pressing shaft 310 is formed to contact an end of the foam F sample so that the foam F sample in the foam sample extracting part 140 may move toward the grinding plate 210, and is supported by the third body 130 when it maximally moves toward an outside direction (the right direction in the drawings) of the body 100.

Since pressure in the body 100 may rapidly change due to the movement of the pressing shaft 310, when a change in the entire pressure is to be measured, the pressure should be measured without changing a position of the pressing shaft 310.

In addition to an example shown in the accompanying drawings, various configurations allowing the pressing shaft 310 to move in the left and right directions in the accompanying drawings to thereby appropriately press and grind the foam F may be used.

The purge gas injecting part 400 injects purge gas into the body 100 to thereby purge the inside thereof, and is preferably formed in the second body 120.

More specifically, the purge gas injecting part 400 may be configured to include a purge gas storing part 410 storing purge gas therein, a flow controlling part 420 controlling the supply flow of the purge gas, and a first valve 430.

Here, the purge gas is gas that is not included in the foam F. As the purge gas, gas that does not react with the air or the gas in the foam F should be used. Typically, helium gas may be used.

The gas discharging part 500 discharges the purge gas injected through the purge gas injecting part 400 or the gas in the foam F, and is preferably formed in the third body 130.

The gas discharging part 500 is connected to a second valve 510 controlling the discharging of the gas. Thereafter, it may be directly connected to an analyzing device 700 performing an analyzing operation. Here, as the analyzing device 700, a precision gas mass spectrometer (Gas/MS) may be used.

When the purge gas is injected by the purge gas injecting part 400, both of the first and second valves 430 and 510 are opened, such that the purge gas flows in the body 100 and is discharged together with residual gas in the body 100, or the like, through the gas discharging part 500, as shown in FIG. 6.

A purge operation by the purge gas injecting part 400 is performed before a grinding operation, thereby making it possible to further increase reliability of the analyzing method.

The pressure gauge 600 measures pressure in the body 100. An example in which the pressure gauge 600 is connected to the purge gas injecting part 400 is shown in the drawings.

Meanwhile, a method of analyzing gas samples in a foam F according to the present invention includes: a) a purging step; b) a foam F sample inserting step; c) a pressure controlling step; d) a grinding step; e) a pressure measuring step; and f) an analyzing step.

The purging step (a) is a step of discharging gas remaining in the body 100. At this step, the first valve 430 of the purge gas injecting part 400 and the second valve 510 of the gas discharging part 500 are opened, thereby purging the inside of the body 100 while allowing the purge gas to flow therein as shown in FIG. 5.

The purging step (a) may be performed for about five to fifteen minutes. A time for which the purging step (a) is performed may be changed according to a size of the body 100, or the like.

During the purging step (a), it is preferable that the pressing shaft 310 is positioned at the rightmost portion in the drawings, such that the purging by the purge gas is smoothly performed.

The foam F sample inserting step (b) is a step of extracting the foam (F) sample as shown in FIG. 4 and inserting the foam sample extracting part 140 including the extracted foam (F) sample therein into the foam receiving part 121 of the second body 120 as shown in FIG. 6.

At this step, the first valve 430 is opened to allow the purge gas to continuously flow in the body 100 and be discharged therefrom, thereby preventing external gas from flowing in the body 100 in an opposite direction to a discharged direction of the purge gas.

The pressure controlling step (c) is a step of controlling pressure in the body to be in an atmospheric pressure state after the second and third bodies 120 and 130 are coupled to each other. At this step, the first valve 430 of the purge gas injecting part 400 and the second valve 510 of the gas discharging part 500 are closed while confirming the pressure in the body 100 through the pressure gauge 600, thereby controlling the pressure in the body 100 to be in the atmospheric pressure state.

The pressure controlling step (c), which is a step of controlling the pressure in the body to be in a reference pressure state of atmospheric pressure before grinding the foam F sample, may be performed by controlling a time point of closure of the first and second valves 430 and 510.

The grinding step (d) is a step of grinding the foam F by operating the pressing part 300 and the grinding part 200. Most of the cells in the foam F are destroyed through the grinding step (d), such that gas existing in the cell exists in the body 100.

The pressure measuring step (e) is a step of measuring pressure by the foam F after the grinding step is completed. At this step, a position of the pressing part 300 is controlled to be in an initial state before the pressing part 300 is operated, thereby allowing a space in the body 100 to be the same as a state before the grinding step, and the pressure is then measured.

A change in the pressure measured at the pressure measuring step (e) may be used as basic data capable of recognizing a degree of the cells existing in a vacuum state in which the gas does not exist in the foam F. Thereafter, the pressure measured at the pressure measuring step (e) is compared with pressure measured using the analyzing device 700, such that it may be used as data capable of evaluating reliability of the analyzing method according to the present invention.

The analyzing step (f) is a step of analyzing the gas samples in the foam by connecting the analyzing device 700 to the gas discharging part 500 and then opening the second valve 510. In the analyzing method using the apparatus 1000 of collecting gas samples in a foam F according to the present invention, the analyzing device 700 is directly connected to the gas discharging part 500 of the apparatus 1000 of collecting gas samples to perform the analysis, thereby making it possible to obtain a result having higher reliability.

As shown in FIG. 7, since the first valve 430 is closed, the gas in the body 100 moves as represented by an arrow to thereby be analyzed by the analyzing device 700.

As described above, in the analyzing method according to the present invention, the foam F is grinded to destroy most of the cells in the foam, thereby making it possible to effectively collect the gas samples, and polluted gas in the body 100 is discharged to the outside and pressure before and after the grinding are measured, thereby making it possible to increase reliability of the analysis.

Particularly, in the case in which the foam F is a urethane foam, the apparatus 1000 of collecting gas samples in a foam F and the analyzing method according to the present invention analyze the gas samples in the urethane foam, thereby making it possible to accurately predict heat insulating characteristics of the urethane foam.

The present invention is not limited to the above-mentioned exemplary embodiments, and may be variously applied, and may be variously modified without departing from the gist of the present invention claimed in the claims.

The invention claimed is:

1. An apparatus for collecting gas samples in a foam, the apparatus comprising:
    a body having a foam receiving part formed therein so that the foam is received therein;
    a grinding part formed to contact one side of the foam in the body, thereby grinding the foam;
    a pressing part formed to contact the other side of the foam in the body, thereby pressing the foam toward the grinding part;
    a purge gas injecting part formed at one side of the body to thereby inject purge gas into the body and having a first valve formed therein;
    a gas discharging part formed at one side of the body to thereby discharge gas in the body to the outside and having a second valve formed therein; and
    a pressure gauge measuring pressure in the body,
    wherein the body is formed by coupling a first body including the grinding part, a second body having the foam receiving part formed therein, and a third body including the pressing part, and
    wherein the foam receiving part of the second body has a foam sample extracting part inserted thereinto, the foam sample extracting part extracting a foam sample to thereby include the foam therein.

2. The apparatus of claim 1, wherein the second and third bodies can be decoupled from each other.

3. The apparatus of claim 1, wherein the foam sample extracting part has a protrusion part formed so as to protrude outwardly from one side end thereof, and the second body has a stepped part formed therein, the stepped part having the protrusion part seated therein to thereby limit an insertion depth of the foam sample extracting part.

4. The apparatus of claim 1, wherein the grinding part includes a grinding plate, a grinding plate support part supporting the grinding plate, and a grinding plate driving part connected to the grinding plate support part to thereby rotate the grinding plate.

5. The apparatus of claim 4, wherein the second body is positioned so that the foam receiving part is eccentric to the grinding plate.

6. The apparatus of claim 4, wherein the pressing part includes a pressing shaft, a rail having the first body fixed thereto, a pressing shaft fixing part connected to the rail and fixing the pressing shaft thereto, and a pressing shaft driving part moving the pressing shaft and the pressing shaft fixing part along the rail.

7. The apparatus of claim 1, wherein the purge gas injecting part is formed in the second body, and the gas discharging part is formed in the third body.

8. The apparatus of claim 7, wherein the purge gas injecting part further includes a purge gas storing part and a flow controlling part.

9. The apparatus of claim 7, wherein the purge gas is helium (He).

10. The apparatus of claim 1, wherein the gas discharging part is directly connected to an analyzing device.

11. A method of analyzing gas samples in a foam using the apparatus of claim 8, the method comprising:
   a) a purging step of opening the first valve of the purge gas injecting part and the second valve of the gas discharging part, thereby allowing the purge gas to purge the inside of the body;
   b) a foam sample inserting step of inserting the foam sample extracting part extracting the foam sample into the foam receiving part of the second body after the second and third bodies and are decoupled from each other;
   c) a pressure controlling step of controlling pressure in the body to be in an atmospheric pressure state after the second and third bodies and are coupled to each other;
   d) a grinding step of grinding the foam by operating the pressing part and the grinding part;
   e) a pressure measuring step of controlling a position of the pressing part to be in an initial state to thereby allow a space in the body to be the same as a state before the grinding step and then measuring the pressure using the pressure gauge; and
   f) an analyzing step of analyzing the gas samples in the foam by connecting the analyzing device to the gas discharging part and then opening the second valve.

* * * * *